(12) United States Patent
Wang et al.

(10) Patent No.: US 11,120,547 B2
(45) Date of Patent: Sep. 14, 2021

(54) RECONSTRUCTION OF IMAGES FROM AN IN VIVO MULTI-CAMERA CAPSULE WITH TWO-STAGE CONFIDENCE MATCHING

(71) Applicant: CapsoVision, Inc., Saratoga, CA (US)

(72) Inventors: Kang-Huai Wang, Saratoga, CA (US); Chenyu Wu, Sunnyvale, CA (US)

(73) Assignee: CAPSOVISION, INC., Saratoga, CA (US)

( * ) Notice: Subject to any disclaimer, the term of this patent is extended or adjusted under 35 U.S.C. 154(b) by 336 days.

(21) Appl. No.: 16/393,894

(22) Filed: Apr. 24, 2019

(65) Prior Publication Data

US 2019/0266724 A1 Aug. 29, 2019

Related U.S. Application Data

(63) Continuation-in-part of application No. 15/306,475, filed as application No. PCT/US2015/027813 on Apr. 27, 2015, now abandoned.

(60) Provisional application No. 62/006,257, filed on Jun. 1, 2014.

(51) Int. Cl.
*G06T 7/00* (2017.01)
*G06T 7/33* (2017.01)
*G06K 9/62* (2006.01)
*A61B 1/00* (2006.01)
*G06T 3/40* (2006.01)
*H04N 5/262* (2006.01)
(Continued)

(52) U.S. Cl.
CPC .......... *G06T 7/0012* (2013.01); *A61B 1/0005* (2013.01); *A61B 1/00009* (2013.01); *A61B 1/041* (2013.01); *G06K 9/6202* (2013.01); *G06T 3/0068* (2013.01); *G06T 3/4038* (2013.01); *G06T 7/33* (2017.01); *H04N 5/2624* (2013.01); *G06T 2207/10068* (2013.01); *G06T 2207/30092* (2013.01); *G06T 2207/30168* (2013.01); *G06T 2207/30242* (2013.01)

(58) Field of Classification Search
None
See application file for complete search history.

(56) References Cited

U.S. PATENT DOCUMENTS

2007/0031062 A1* 2/2007 Pal ..................... H04N 5/23238
382/284
2008/0240613 A1* 10/2008 Dietz .................. G02B 21/367
382/284
(Continued)

*Primary Examiner* — John P Leubecker
(74) *Attorney, Agent, or Firm* — Blairtech Solution LLC

(57) ABSTRACT

A method and apparatus of image stitching using confidence level of image matching on image pair to be stitched are disclosed. According to the present invention, the first quality of image matching is determined for a current image based on feature matching on first image pairs corresponding to the current image and a neighboring image set. If the first quality of image matching for at least one first image pair satisfies a first quality criterion, then the second quality of image matching is determined based on pixel-domain matching for one or more candidate image pairs, where each candidate image pair has a corresponding first quality of image matching satisfying the first quality criterion. If the second quality of image matching for a candidate image pair satisfies a second quality criterion, then the matched image pair is stitched.

18 Claims, 2 Drawing Sheets

(51) Int. Cl.
*G06T 3/00* (2006.01)
*A61B 1/04* (2006.01)

(56) References Cited

U.S. PATENT DOCUMENTS

| | | | | |
|---|---|---|---|---|
| 2009/0278921 | A1* | 11/2009 | Wilson | A61B 1/045 |
| | | | | 348/77 |
| 2010/0149183 | A1 | 6/2010 | Loewke et al. | |
| 2010/0194992 | A1* | 8/2010 | Kouno | G11B 27/28 |
| | | | | 348/700 |
| 2010/0277650 | A1* | 11/2010 | Matsuzaki | G06T 7/246 |
| | | | | 348/700 |
| 2011/0249910 | A1* | 10/2011 | Henderson | G06K 9/00134 |
| | | | | 382/278 |
| 2012/0154562 | A1 | 6/2012 | Munzenmayer et al. | |
| 2013/0109915 | A1* | 5/2013 | Krupnik | G06F 3/0482 |
| | | | | 600/109 |
| 2014/0376792 | A1* | 12/2014 | Matsuzaki | A61B 1/00009 |
| | | | | 382/128 |
| 2014/0376817 | A1* | 12/2014 | Yaguchi | G06K 9/00751 |
| | | | | 382/195 |
| 2015/0045619 | A1* | 2/2015 | Kumar | A61B 1/0005 |
| | | | | 600/109 |
| 2015/0221116 | A1* | 8/2015 | Wu | A61B 1/00009 |
| | | | | 382/128 |
| 2018/0085002 | A1* | 3/2018 | Glinec | A61B 1/24 |

* cited by examiner

RECONSTRUCTION OF IMAGES FROM AN IN VIVO MULTI-CAMERA CAPSULE WITH TWO-STAGE CONFIDENCE MATCHING

CROSS REFERENCE TO RELATED APPLICATIONS

The present invention is a continuation-in-part of and claims priority to U.S. patent application Ser. No. 15/306,475, filed on Oct. 24, 2016, now abandoned which is U.S. National Stage under 35 USC 371 of and claims priority to PCT/US2015/027813, filed on Apr. 27, 2015, which claims priority to U.S. Provisional Patent Application, Ser. No. 62/006,257, filed on Jun. 1, 2014. The U.S. Non-Provisional Patent Application, PCT Application and U.S. Provisional Application are hereby incorporated by reference in their entirety.

FIELD OF THE INVENTION

The present invention relates to image stitching from images captured using in vivo capsule camera and their display thereof.

BACKGROUND AND RELATED ART

Capsule endoscope is an in vivo imaging device, which addresses many of problems of traditional endoscopes. A camera is housed in a swallowable capsule along with a radio transmitter for transmitting data to a base-station receiver or transceiver. A data recorder outside the body may also be used to receive and record the transmitted data. The data primarily comprises images recorded by the digital camera. The capsule may also include a radio receiver for receiving instructions or other data from a base-station transmitter. Instead of using radio-frequency transmission, lower-frequency electromagnetic signals may be used. Power may be supplied inductively from an external inductor to an internal inductor within the capsule or from a battery within the capsule. In another type of capsule camera with on-board storage, the captured images are stored on-board instead of transmitted to an external device. The capsule with on-board storage is retrieved after the excretion of the capsule. The capsule with on-board storage provides the patient the comfort and freedom without wearing the data recorder or being restricted to proximity of a wireless data receiver.

While forward-looking capsule cameras include one camera, there are other types of capsule cameras that use multiple cameras to provide side view or panoramic view. A side or reverse angle is required in order to view the tissue surface properly. It is important for a physician or diagnostician to see all areas of these organs, as polyps or other irregularities need to be thoroughly observed for an accurate diagnosis. A camera configured to capture a panoramic image of an environment surrounding the camera is disclosed in U.S. patent application Ser. No. 11/642,275, entitled "In vivo sensor with panoramic camera" and filed on Dec. 19, 2006.

In an autonomous capsule system, multiple images along with other data are collected during the course when the capsule camera travels through the gastrointestinal (GI) tract. The images and data after being acquired and processed are usually displayed on a display device for a diagnostician or medical professional to examine. However, each image only provides a limited view of a small section of the GI tract. It is desirable to form a large picture from multiple capsule images representing a single composite view. For example, multiple capsule images may be used to form a cut-open view of the inner GI tract surface. The large picture can take advantage of the high-resolution large-screen display device to allow a user to visualize more information at the same time. The image stitching process may involve removing the redundant overlapped areas between images so that a larger area of the inner GI tract surface can be viewed at the same time as a single composite picture. In addition, the large picture can provide a complete view or a significant portion of the inner GI tract surface. It should be easier and faster for a diagnostician or a medical professional to quickly spot an area of interest, such as a polyp.

In the field of computational photography, image mosaicing techniques have been developed to stitch smaller images into a large picture. A review of general technical approaches to image alignment and stitching can be found in "Image Alignment and Stitching: A Tutorial", by Szeliski, Microsoft Research Technical Report MSR-TR-2004-92, Dec. 10, 2006.

For image mosaicing, corresponding parts, objects or areas among images are identified first. After corresponding parts, objects or areas are identified, in other words, after two images are registered, they can be stitched by aligning the corresponding parts, objects or areas. Two images can be registered directly in the pixel domain or matched based on features extracted from images. The pixel-based image matching is also called direct match. There are several similarity measurements that can be used for evaluating the quality of image matching, such as sum of squared distance (SSD), normalized cross correlation (NCC), mutual information (MI) etc. NCC is equivalent to SSD if we apply normalization to SSD. Specifically, to match images from two different modalities, the mutual information of images A and B is defined as:

$$I(A, B) = \sum_{a,b} p(a, b) \log\left(\frac{p(a, b)}{p(a)p(b)}\right). \quad (1)$$

The mutual information measures the distance between the joint distribution of the images intensity values p(a,b) and the joint distribution of the images intensity values when they are independent, p(a)p(b). It is a measure of dependence between two images. The assumption is that there is maximal dependence between the intensity values of the images when they are correctly aligned. Mis-registration will result in a decrease in the measure of mutual information. Therefore, larger mutual information implies more reliable registration.

The feature-based matching first determines a set of feature points in each image and then compares the corresponding feature descriptors. To match two image patches or features captured from two different viewing angles, a rigid model including scaling, rotation, etc. is estimated based on the correspondences. To match two images captured deforming objects, a non-rigid model including local deformation can be computed.

The number of feature points is usually much smaller than the number of pixels of a corresponding image. Therefore, the computational load for feature-based image matching is substantially less that for pixel-based image matching. However, it is still time consuming for pair-wise matching. Usually k-d tree, a well-known technique in this field, is utilized to speed up this procedure. Accordingly, feature-based image matching is widely used in the field. Nevertheless, the feature-based matching may not work well for images under some circumstances. In this case, the direct image matching can always be used as a fall back mode, or a combination of the above two approaches may be preferred.

Image matching techniques usually assume certain motion models. When the scenes captured by the camera consist of rigid objects, image matching based on either feature matching or pixel domain matching will work reasonably well. However, if the objects in the scene deform or lack of distinguishable features, it would make the image matching task very difficult. For capsule images captured during the course of travelling through the GI track, the situation is even more challenging. Not only the scenes corresponding to walls of the GI track deform while camera is moving and often are lack of distinguishable features, but also the scenes are captured with a close distance from the camera. Due to the close distance between objects and the camera, the often used linear camera model may fail to produce good match between different scenes. In addition, light reflection from near objects may cause over exposure for some parts of the object. Therefore, it is desirable to develop methods that can overcome the issues mentioned above.

SUMMARY OF INVENTION

A method of adaptively displaying images of human GI (gastrointestinal) tract captured using a capsule camera when the capsule camera travelled through the human GI tract is disclosed. While image stitching provides an efficient viewing or examination of a large number of images, image stitching may cause noticeable artifacts particularly for images that do not fit camera models well. The present invention utilizes the quality of feature-based image matching to guide whether to stitch underlying images or not. Accordingly, an improved image reconstruction and a more visually pleasant viewing can be achieved. The feature-based image matching is computational efficient. However, the capsule images of the human gastrointestinal tract are often noisy and lack of distinct features, which cause the feature-based image matching unreliable. In order to overcome the issues mentioned above, a method of image matching to achieve very high confidence level for capsule images of the human GI tract is disclosed in the present invention.

According to embodiments of the present invention, a plurality of images captured by the camera is received and the quality of image matching for each pair of images is determined. The first quality of image matching is determined for a current image based on feature matching for first image pairs. Each of the first image pairs corresponds to the current image and one neighboring image in a neighboring image set of the current image, and each neighboring image in the neighboring image set corresponds to an unstitched image from the plurality of images captured by the capsule camera or one previously stitched image close to the current image temporally. If the first quality of image matching for at least one first image pair satisfies a first quality criterion, then the second quality of image matching is determined based on pixel-domain matching for one or more candidate image pairs, where each candidate image pair has a corresponding first quality of image matching satisfying the first quality criterion. If the second quality of image matching for at least one candidate image pair satisfies a second quality criterion, then the current image is designated as one matched image; and said one matched image is stitched with a selected neighboring image to form one stitched image larger than the current image, where the selected neighboring image corresponds to one candidate image pair with the second quality of image matching satisfying the second quality criterion.

In one embodiment, the first quality of image matching is based on features extracted between two images of each first image pair. Furthermore, the first quality of image matching is based on posterior probability corresponding to correct image matching for each of the features, wherein each of the features is modelled as a binary random variable being an inlier or an outlier. The first quality of image matching can be measured by counting a number of the features being the inlier, and the first quality criterion corresponds to the number of the features being to the inlier being greater than a first threshold. The first threshold can be dependent on a first probability corresponding to one feature being the inlier and a second probability corresponding to one feature being the outlier. The method may further comprise, for a target candidate image pair, determining one transform model for two images of the target candidate image pair based on the features extracted for said two images of the target candidate image pair and the features belong to the inlier. The transform model is applied to the target candidate image pair prior to said determining the second quality of image matching for the target candidate image pair.

If the first quality of image matching for none of the first image pairs satisfies the first quality criterion or if the second quality of image matching for none of said one or more candidate image pairs satisfies the second quality criterion, the current image is designated as one unmatched image. One or more stitched pictures and one or more unmatched images can be displayed on a display device in an interleaved manner, where said one or more stitched pictures are displayed during first periods and said one or more unmatched images are displayed during second periods, and the first periods and the second periods are non-overlapping. Alternatively, one or more stitched pictures can be displayed in a first display area on a display device and one or more unmatched images can be displayed in a second display area on the display device.

The second quality of image matching can be based on a sum of squared distance (SSD), normalized cross correlation (NCC) or mutual information (MI) between two images in one candidate image pair. When the second quality of image matching is based on the SSD, the second quality criterion corresponds to the SSD being smaller than a second threshold. When the second quality of image matching is based on the NCC or MI, the second quality criterion corresponds to the NCC or MI being larger than a third threshold.

In one embodiment, said stitching said one matched image with the selected neighboring image is performed only if a number of constituent images for the selected neighboring image is less than a fourth threshold.

DETAILED DESCRIPTION OF THE INVENTION

Figure 1:
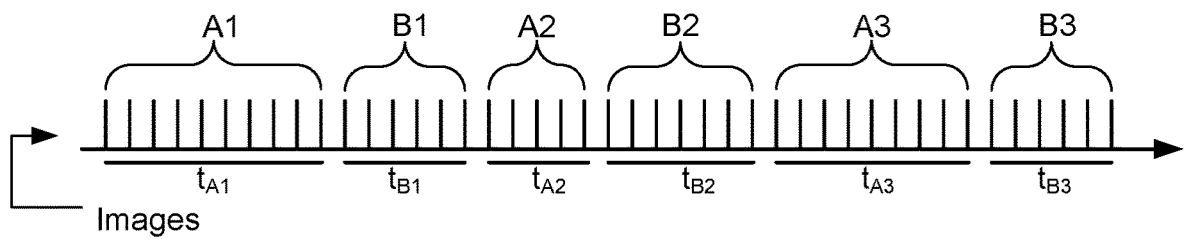
FIG. 1 illustrates an exemplary high-confidence and low-confidence image pair's determination based on image matching, and displaying the high-confidence matched and unmatched low-confidence images in the same display area in an interleaved manner according to an embodiment of the present invention.
Figure 1:
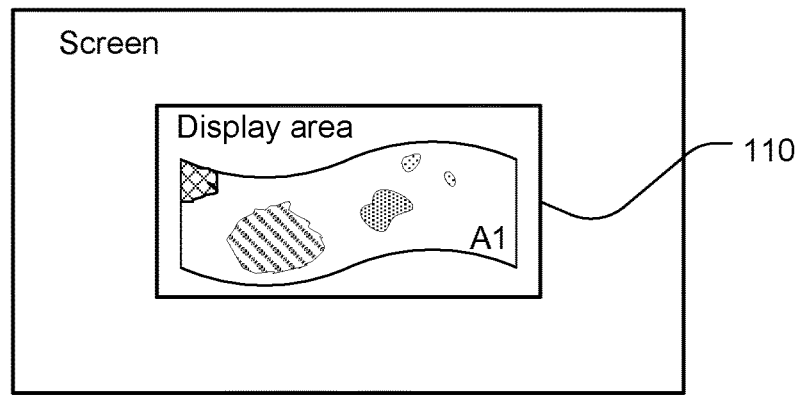

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely a representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

As mentioned before, image matching may not work well for images under some circumstances, particularly for images captured using a capsule image through the human gastrointestinal (GI) track. Embodiments according to the present invention use a quality measure of image matching. According to the measured matching quality, a matching confidence level is determined. When the matching confidence level is good enough, the underlying images are stitched. Otherwise, the underlying images are not stitched. For example, if feature based image matching is used, image matching will be performed to match many correspondences. After matching, RANdom Sample Consensus (RANSAC) process will be used to select a set of inliers that are compatible with a transformation model between the images. RANSAC is a well-known technique in the field that is used to find a best transform among feature points between two images. In order to verify the match, a confidence score is calculated based on a probabilistic model.

For each pair of matching images, a subset of feature correspondences that are geometrically consistent (i.e., RANSAC inliers), and the remaining features are not consistent (i.e., RANSAC outliers). To verify the set of correspondences, the probabilities that the set of features is generated by correct image matching (i.e., inliers) or by false image matching (i.e., outliers) are evaluated. For a given image, the total number of features is denoted as $n_f$ and the number of inliers is denoted as $n_i$, the event that image matching correctly/incorrectly is represented by a binary variable $m \in \{0,1\}$, where m=1 represents correct match and m=0 represents incorrect match. The event that the $i^{th}$ feature correspondence is an inlier/outlier, represented by the binary variable $f^{(i)} \in \{0,1\}$, where f=1 represents inlier and f=0 represents outlier, is assumed to be an independent Bernoulli distribution. Accordingly, the probability of all features being inliers is Binomial distribution:

$$p(f^{(1:n_f)}|m=1) = B(n_i; n_f, p_1), \text{ and} \quad (2)$$

$$p(f^{(1:n_f)}|m=0) = B(n_i; n_f, p_0), \quad (3)$$

where $p_1$ is the probability that a feature is an inlier given correct image matching, and $p_0$ is the probability that a feature is an inlier given false image matching. The total number of inliers, is calculated according to $n_i = \sum_{i=1}^{n_f} f^{(i)}$. The posterior probability that image matching is correct can be evaluated using Bayes's Rule:

$$\begin{aligned} p(m=1|f^{(1:n_f)}) &= p(f^{(1:n_f)}|m=1)p(m=1)/p(f^{(1:n_f)}) \\ &= 1/(1 + p(f^{(1:n_f)}|m=0)p(m=0)/ \\ &\quad p(f^{(1:n_f)}|m=1)p(m=1)) \end{aligned} \quad (4)$$

Let the event of images matching correctly/incorrectly be a uniform prior (i.e., a prior probability distribution), p(m=0)=p(m=1). A criterion to accept image matching is based on whether $p(m=1|f^{(1:n_f)}) > p_{min}$, where $p_{min}$ is a minimum probability threshold used as a criterion to accept the image matching. Through a sequence of mathematically derivation, this condition is reduced to a likelihood ratio test:

$$B(n_i; n_f, p_1)/B(n_i; n_f, p_0) \begin{array}{c} \text{accept} \\ > \\ < \\ \text{reject} \end{array} \frac{1}{1/p_{min} - 1}, \text{ and} \quad (5)$$

$$B(n_i; n_f, p_1) = \binom{n_f}{n_i} p_1^{n_i} (1-p_1)^{n_f - n_i} \quad (6)$$

The values for $p_{min}$, $p_1$ and $p_0$ can be properly chosen according to image models or based on test data. The above decision process can be further simplified as the following testing:

$$n_i > g(n_f). \quad (7)$$

where g is a function of $p_{min}$, $p_1$ and $p_0$. In other words, after the values for $p_{min}$, $p_1$ and $p_0$ are determined, g can be determined. The decision process simply becomes counting the number of inlier, $n_i$. If the condition of eqn. (7) is satisfied, the image matching is verified and the registration is declared as confident registration. Otherwise, the image matching is not verified and the registration has low confidence. In the above embodiment, the quality of image matching is measured in terms of the posterior probability that image matching is correct given the features extracted as shown in eqn. (4). If the quality of image matching is over a threshold (i.e., $p_{min}$), the image matching is verified. After further derivation, the decision process according to one embodiment of the present invention simply becomes counting the number of inlier, $n_i$, and comparing the result with a threshold. While the quality of image matching can be measured by counting the number of inlier, the quality of image matching can be measured by counting the number of outlier. In this case, if the number of outlier is less than a second threshold, the image matching is verified. Otherwise, image matching is not verified.

Under ideal conditions where the image contents include solid object with very distinct features, the feature based image matching should perform well. However, the images are often captured in a noisy environment by the capsule camera during the capsule camera travelled through the human gastrointestinal (GI) tract. Furthermore, the images for the GI tract are often lack of distinct features. The feature based image matching may not work properly. If a pair of features between two images are incorrected matches, the stitched image may show noticeable artifacts. In order to overcome this issue, the present invention uses a two-stage image matching to improve the confidence level of image matching. In one embodiment, the feature based image matching is used as the first-stage image matching. If the quality of image matching satisfies a quality criterion, a second-stage image matching is performed in the pixel domain. If the quality of the second-stage image matching satisfies a second quality criterion, the image match is confirmed and the target image can then be stitched with the match image.

The pixel-domain-based image matching works on the pixel data directly and is presumably more reliable. However, the pixel-domain-based image matching is more computational intensity. The present invention uses the pixel-domain-based image matching for further confirmation of good image matching. The operations are only applied to the image pairs that show good matching during the first-stage matching. Therefore, the computational complexity associated with the pixel-domain-based image matching The capsule images represent images captured by the capsule camera in a dynamic environment of the human GI tract. For example, while travelling along the GI tract, the camera may tilt and rotate. In addition, the GI tract wall may deform. Therefore, during image matching, the contents in two images have to be transformed for identifying corresponding features or pixels. For a given image pair, it would require substantial computations to identify a best transform model. However, the transform model can be derived based on the features extracted from the image pair to reduce the required computations. The transform model derived can then be applied to the image pairs prior to the second-stage image matching based on the pixel domain.

For the pixel-domain image matching, the system uses non-feature based direct matching. For example, the system may calculate the sum of squared distance (SSD) as the measure of quality of image matching. The SSD between images A and B is defined as:

$$D_{SSD}(A, B|T) = \Sigma_{(x,y)}(A(x,y) - B(T(x,y)))^2, \quad (7)$$

where (x,y) is the pixel in the overlap area, T is the transformation from image A to B. By carefully choosing a threshold Dmax, if Dssd(A,B|T)<Dmax, the image matching can be verified and the registration has high confidence. Otherwise the registration is not verified and the registration is not confident.

In another embodiment normalized cross correlation (NCC) or mutual information (MI) can be used as a criterion to evaluate the quality of matching and compute the confidence score.

In another embodiment, in order to stitch two sequential images, each image of the pair will be down-sampled to create image pyramids first. From the coarse level, a global transformation will be estimated using exhaustive search within a pre-defined range. The resulting global transformation will be refined in the next level until the final level, which is the original image. After the global transformation is estimated, a free-form deformation transformation can be applied to the overlapped area to estimate the local deformation. The output of the optimization object function can be used as a criterion to evaluate the quality of matching and compute the confidence score.

In another embodiment, in order to stitch two sequential images, each image of the pair will be down-sampled to create image pyramids first. From the coarse level, a global transformation will be estimated by averaging the local transformation, which is computed by applying free-form deformation to the entire image. The resulting global transformation will be refined in the next level until the final level, which is the original image. Such a procedure will be iterated until the process converges to eliminate outlier effect. After the global transformation is estimated, a free-form deformation transformation can be applied to the overlapped area to estimate the local deformation. The output of the optimization object function can be used as a criterion to evaluate the quality of matching and compute the confidence score.

The image matching can be performed for a given image, where an image pair is formed based on the given image and a neighboring image of the given image. The image matching can be checked for multiple image pairs of the given image, where each pair corresponds to the given image and one neighboring image belonging to a neighboring image set of the given image. For example, the given image corresponds to the image with index i and the neighboring image set include images with indexes from (i−1) to (i−N) and from (i+1) to (i+N). The image matching can be searched from the closest neighboring image to the farthest neighboring image (e.g. (i+1), (i−1), (i+2), (i−2), . . . , (i−N)). If image matching with high confidence is found between the given image and one neighboring image, the two images are stitched to form a stitched image. The stitched image is inserted into the image sequence to replace the given image and the matched neighboring image. The two-stage image matching process is then applied to the sequence with the given image and the matched neighboring image replaced by the stitched image. The process can be iterated until no matching can be found for the image pairs between a given image and a neighboring image in the neighboring image set. In this case, the image matching process moves to the next given image. The next given image can be set to image (i+1), where the current given image is image i according to one embodiment. In another embodiment, the next given image can be set to image (i+N+1).

In another embodiment, more than two images can be stitched together with high confidence if and only if the following condition is true. Given the set of images i1, i2, . . . , iN, for each image ij (j=1,2, . . . N), we can find at least one image from the rest of images to match ij with high confidence. There might be multiple images matching ij with high confidence. Otherwise, it means ij cannot be stitched with the rest of images and will be removed from this image set. Above process can be repeated until no image will be removed from the image set. Then all the images in this set can be stitched together to form a large composite image. All the removed images will be displayed individually.

In one embodiment example, i1, i2, . . . iN are a sequence of images along time domain, where i1, i2, i3, i5, i6, i7, i8, i12 are found to find match with high confidence and are stitched together and displayed as composite image I1, while i4, i9, i10 and i11 could not and are displayed as single images. If i4 and i9 and i11 could find match with confidence while i10 could not, then i4, i9 and i11 are stitched together as a composite image I2 and displayed as such while i10 is displayed as single image in the video separately.

Sometimes the advantage of stitching too few images and displaying them in one composite image is outweighed by the disadvantage. For example the stitched images have arbitrary size while single image is fixed in dimensions and aspect ratio so looking at two stitched images in a composite image may not be as efficient in time compared with reading these two images in a video displayed at certain frame rate. A threshold T may be chosen to set the minimum number of images matched with high confidence before they are stitched and displayed as a composite image.

The quality of image matching disclosed above can be used to guide image stitching. When the quality of image matching is high, the registration can be declared to be confident. In one embodiment, the images are stitched to form a larger composite picture for images with high confidence even if there are discontinuities along transit time. For those images declared to be low confidence, the images are not stitched. The un-stitched images are treated as individual images or an image sequence and viewed as video. FIG. 1 illustrates one embodiment according to the present invention, where A1, A2 and A3 represent three groups of images with high confidence throughout the video. Each of A1, A2 and A3 corresponds to images in respective time periods $t_{A1}$, $t_{A2}$ and $t_{A3}$ having high confidence. The images within each group (i.e., A1, A2 or A3) are stitched into one or more larger composite pictures. B1, B2 and B3 correspond to images in respective time periods $t_{B1}$, $t_{B2}$ and $t_{B3}$ having low confidence. In one embodiment, images associated with A1, A2, A3 can be displayed in display area 110, and then then followed by images associated with B1, B2 and B3. FIG. 1 illustrates an instance that composite picture corresponding to group A1 is being displayed. The display order can be A1, A2 and A3 and then followed by B1, B2 and B3. The display may also follow the order of A1, B1, A2, B2, A3 and B3. When images associated with A1, A2, A3 are displayed, a stitched larger image or images can be used to allow a view to examine multiple images at the same time. When images associated with B1, B2 and B3 are displayed, the images will be treated as individual images and they can be displayed one by one manually or displayed as a video sequence at a desirable playback rate. The images are taken at uniform speed in FIG. 1. In another embodiment, images could be taken at non-uniform frame rate.

Figure 2:
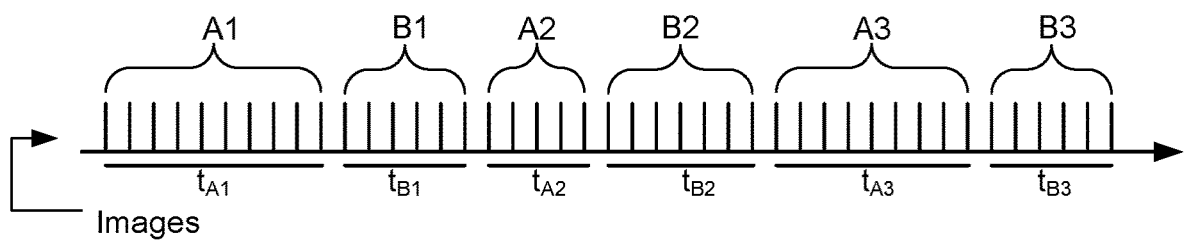
FIG. 2 illustrates an exemplary high-confidence and low-confidence image pair's determination based on image matching, and displaying the high-confidence matched and low-confidence unmatched images in respective display areas according to an embodiment of the present invention.
Figure 2:
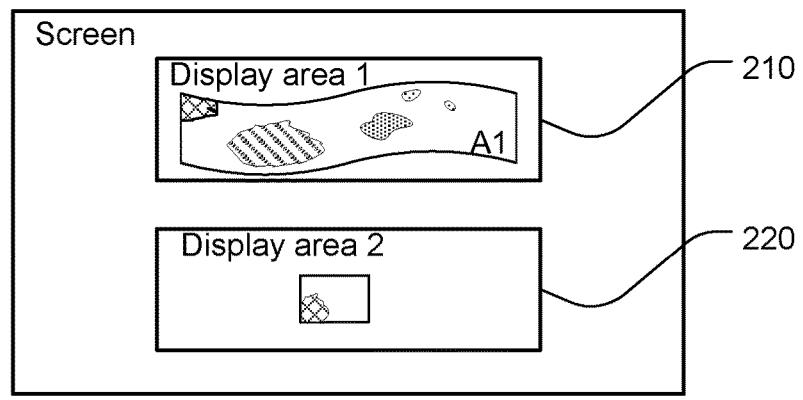

FIG. 2 illustrates another embodiment according to the present invention. Again, A1, A2 and A3 represent images with high confidence throughout the video. B1, B2 and B3 correspond to images having low confidence. There are two display areas, one is used to display A1, A2 and A3, the other one is used to display B1, B2 and B3. Two display areas (210 and 220) are used to display A1/A2/A3 and B1/B2/B3 separately. Images associated with A1, A2, A3 can be displayed as stitched larger composite in display area 210. Images associated with B1, B2 and B3 can be displayed as individual images. They can be displayed one by one manually or displayed in display area 220 as a video at a desirable play back rate.

Figure 3:
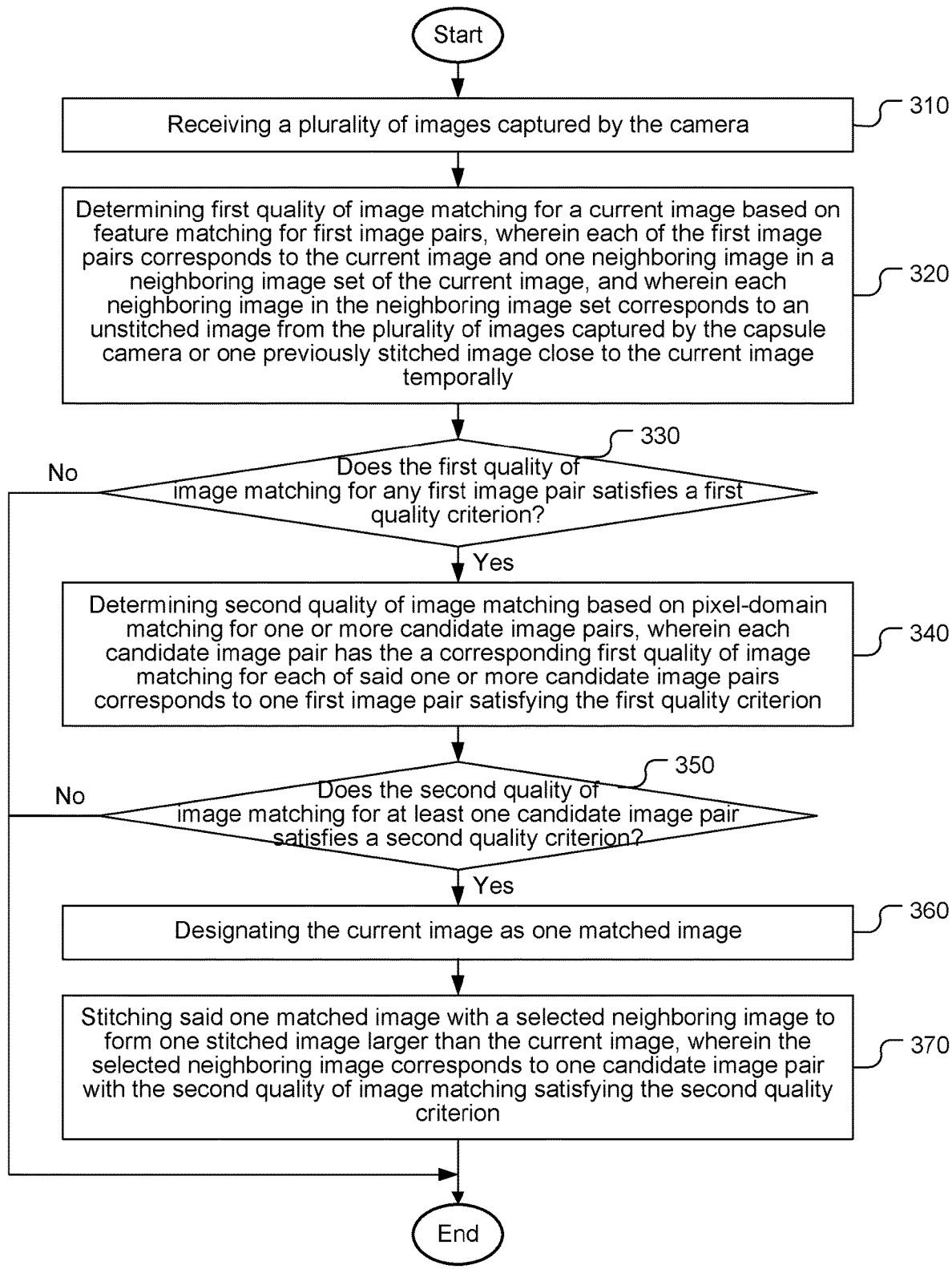
FIG. 3 illustrates an exemplary flowchart for a system for displaying images incorporating image stitching depending on the first quality of image matching based on feature matching and the second quality of image matching based on pixel-domain matching according to embodiments of the present invention.

FIG. 3 illustrates an exemplary flowchart for a system for displaying images incorporating image stitching depending on the first quality of image matching based on feature matching and the second quality of image matching based on pixel-domain matching according to embodiments of the present invention. The steps shown in the flowchart may be implemented as program codes executable on one or more processors (e.g., one or more CPUs) at the encoder side and/or the decoder side. The steps shown in the flowchart may also be implemented based hardware such as one or more electronic devices or processors arranged to perform the steps in the flowchart. According to this method, a plurality of images are captured by the capsule camera in step 310. First quality of image matching for a current image is determined based on feature matching for first image pairs in step 320, where each of the first image pairs corresponds to the current image and one neighboring image in a neighboring image set of the current image, and each neighboring image in the neighboring image set corresponds to an unstitched image from the plurality of images captured by the capsule camera or one previously stitched image close to the current image temporally. Whether the first quality of image matching for at least one first image pair satisfies a first quality criterion is checked in step 330. If the result is "Yes", the process goes to step 340; otherwise (i.e., the "No" path), the process is terminated. In step 340, second quality of image matching is determined based on pixel-domain matching for one or more candidate image pairs, where each candidate image pair has a corresponding first quality of image matching satisfying the first quality criterion. Whether the second quality of image matching for at least one candidate image pair satisfies a second quality criterion is checked in step 350. If the result is "Yes", steps 360 and 370 are performed; otherwise (i.e., the "No" path), the process is terminated.

While specific examples are directed to capsule images, the image stitching based on quality of image matching according to the present invention may also be applied to images of natural scenes captured at different viewing angles.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of displaying images of human GI (gastrointestinal) tract captured using a capsule camera when the capsule camera travelled through the human GI tract, the method comprising:
   receiving a plurality of images captured by the capsule camera;
   determining first quality of image matching for a current image based on feature matching for one or more first image pairs, wherein each of the first image pairs corresponds to the current image and one neighboring image in a neighboring image set of the current image, and wherein each neighboring image in the neighboring image set corresponds to an unstitched image from the plurality of images captured by the capsule camera or one previously stitched image close to the current image temporally;
   when the first quality of image matching for at least one first image pair satisfies a first quality criterion:
      determining second quality of image matching based on pixel-domain matching for one or more candidate image pairs, wherein each candidate image pair has a corresponding first quality of image matching satisfying the first quality criterion; and when the second quality of image matching for at least one candidate image pair satisfies a second quality criterion:

designating the current image as one matched image; and stitching said one matched image with a selected neighboring image to form one stitched image larger than the current image, wherein the selected neighboring image corresponds to one candidate image pair with the second quality of image matching satisfying the second quality criterion.

2. The method of claim 1, wherein the first quality of image matching is based on features extracted between two images of each first image pair.

3. The method of claim 2, wherein the first quality of image matching is based on posterior probability corresponding to correct image matching for each of the features, wherein each of the features is modelled as a binary random variable being an inlier or an outlier.

4. The method of claim 3, wherein the first quality of image matching is measured by counting a number of the features being the inlier, and the first quality criterion corresponds to the number of the features being to the inlier being greater than a first threshold.

5. The method of claim 4, wherein the first threshold is dependent on a first probability corresponding to one feature being the inlier and a second probability corresponding to one feature being the outlier.

6. The method of claim 3, further comprising, for a target candidate image pair, determining one transform model for two images of the target candidate image pair based on the features extracted for said two images of the target candidate image pair and the features belong to the inlier.

7. The method of claim 6, wherein said one transform model is applied to the target candidate image pair prior to said determining the second quality of image matching for the target candidate image pair.

8. The method of claim 1, wherein if the first quality of image matching for none of said one or more first image pairs satisfies the first quality criterion or if the second quality of image matching for none of said one or more candidate image pairs satisfies the second quality criterion, designating the current image as one unmatched image.

9. The method of claim 8, wherein one or more stitched pictures and one or more unmatched images are displayed on a display device in an interleaved manner, wherein said one or more stitched pictures are displayed during first periods and said one or more unmatched images are displayed during second periods, and the first periods and the second periods are non-overlapping.

10. The method of claim 8, wherein one or more stitched pictures are displayed in a first display area on a display device and one or more unmatched images are displayed in a second display area on the display device.

11. The method of claim 1, wherein the second quality of image matching is based on a sum of squared distance (SSD), normalized cross correlation (NCC) or mutual information (MI) between two images in one candidate image pair.

12. The method of claim 11, wherein when the second quality of image matching is based on the SSD, the second quality criterion corresponds to the SSD being smaller than a second threshold.

13. The method of claim 11, wherein when the second quality of image matching is based on the NCC or MI, the second quality criterion corresponds to the NCC or MI being larger than a third threshold.

14. The method of claim 1, wherein said stitching said one matched image with the selected neighboring image is performed only if a number of constituent images for the selected neighboring image is less than a fourth threshold.

15. A system of displaying images of human gastrointestinal (GI) tract captured using a capsule camera when the capsule camera travelled through the GI tract, the system comprising:

a display device; and a processor coupled to the display device, wherein the processor is configured to:

receive a plurality of images captured by the capsule camera;

determine first quality of image matching for a current image based on feature matching for one or more first image pairs, wherein each of the first image pairs corresponds to the current image and one neighboring image in a neighboring image set of the current image, and wherein each neighboring image in the neighboring image set corresponds to an unstitched image from the plurality of images captured by the capsule camera or one previously stitched image close to the current image temporally;

if the first quality of image matching for at least one first image pair satisfies a first quality criterion:

determine second quality of image matching based on pixel-domain matching for one or more candidate image pairs, wherein each candidate image pair has a corresponding first quality of image matching satisfying the first quality criterion; and if the second quality of image matching for at least one candidate image pair satisfies a second quality criterion:

designate the current image as one matched image; and stitch said one matched image with a selected neighboring image to form one stitched image larger than the current image, wherein the selected neighboring image corresponds to one candidate image pair with the second quality of image matching satisfying the second quality criterion.

16. The system of claim 15, wherein if the first quality of image matching for none of the said one or more image pairs satisfies the first quality criterion or if the second quality of image matching for none of said one or more candidate image pairs satisfies the second quality criterion, designating the current image as one unmatched image.

17. The system of claim 16, wherein one or more stitched pictures and one or more unmatched images are displayed on a display device in an interleaved manner, wherein said one or more stitched pictures are displayed during first periods and said one or more unmatched images are displayed during second periods, and the first periods and the second periods are non-overlapping.

18. The system of claim 16, wherein one or more stitched pictures are displayed in a first display area on a display device and one or more unmatched images are displayed in a second display area on the display device.

* * * * *